United States Patent [19]

Fleischhacker et al.

[11] Patent Number: 5,098,392
[45] Date of Patent: Mar. 24, 1992

[54] LOCKING DILATOR FOR PEEL AWAY INTRODUCER SHEATH

[76] Inventors: John J. Fleischhacker; Dennis A. Stowers, both of 14901 Minnetonka Industrial Rd., Minnetonka, Minn. 55345

[21] Appl. No.: 724,405

[22] Filed: Jun. 28, 1991

[51] Int. Cl.[5] .......................................... A61M 5/178
[52] U.S. Cl. .................................... 604/165; 604/161
[58] Field of Search ............... 604/160, 161, 164, 165, 604/264, 280

[56] References Cited

U.S. PATENT DOCUMENTS 2,566,499  9/1951  Richter ................................. 604/161

FOREIGN PATENT DOCUMENTS

WO90/11103  10/1990  PCT Int'l Appl. ................. 604/264
2161709  1/1986  United Kingdom ................ 604/164

Primary Examiner—Cary E. O'Connor
Attorney, Agent, or Firm—Scott R. Cox

[57] ABSTRACT

Locking dilator and peel away introducer sheath assembly for preventing undesired rearward migration of a dilator within an introducer sheath to insure a proper longitudinal relationship. The dilator has secured to its proximal end a gripping clamp for holding securely the handle of the introducer sheath to accommodate placement of the dilator and introducer sheath into an appropriate location within a patient resulting in minimal tissue damage and trauma.

10 Claims, 6 Drawing Sheets

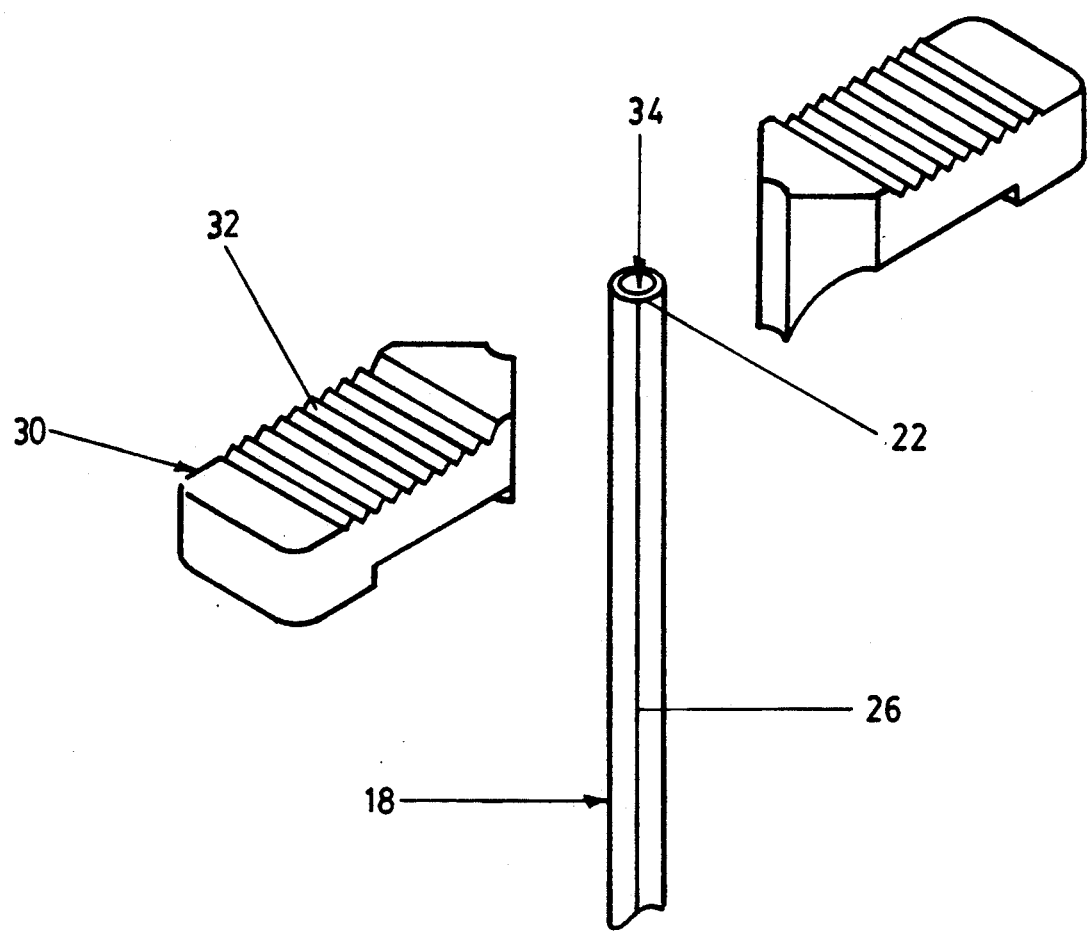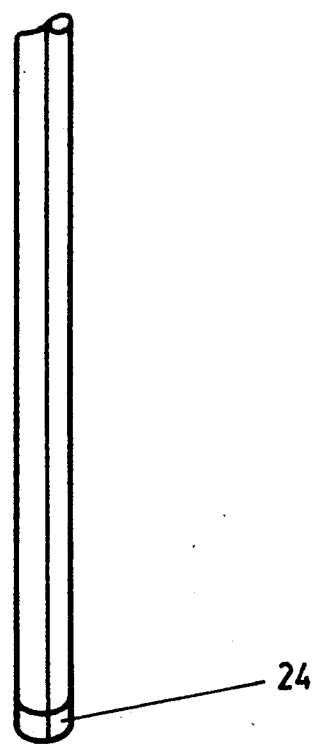
FIG. 4

LOCKING DILATOR FOR PEEL AWAY INTRODUCER SHEATH

BACKGROUND OF INVENTION

1. Field of Invention

This invention relates to invasive medical devices. In particular, this invention relates to a locking dilator associated with a peel away introducer sheath used for the introduction of catheters and other such medical devices into a patient.

2. Prior Art

For many medical purposes it is important to introduce devices through the skin and underlying tissue layers into blood vessels or other locations inside the body of a patient. These purposes include, but are not limited to the introduction of catheters, pacemaker leads and other such devices into a patient's body. These devices are transcutaneous devices which pass through the skin and into the blood vessel during use.

Several methods have been designed to place such devices within the body. Perhaps the earliest method was to cut an opening in the body, insert the device and then close the wound around the device. One example of this method is known as the "cut-down" placement method. Disadvantages are associated with this method because of the high skill necessary for its precise use as well as the specialized medical facilities necessary to perform the procedure safely. Further, because of differences in medical personnel and in patients, trauma, disruptions and infection risks increase to the tissues involved where this method is employed.

To alleviate some of these disadvantages, percutaneous methods have been developed to create small openings in the tissue and then to employ various devices to slightly enlarge the opening to permit the insertion of specialized medical instruments. One such device commonly used is a dilator. The dilator has a tapered end which will enlarge the opening at the puncture site as the dilator is advanced through the tissue. Once the tissue is enlarged, the dilator is removed and the desired catheter or other medical device is quickly inserted through the opening created. This method is subject to many problems because of trauma, bleeding of the patient and the difficulty of insertion of certain specialized medical instruments in such an opening. Besides the possibility of reclosing of the opening prior to insertion of the secondary medical instrument, many types of medical devices, including pacemaker leads are extremely soft and supple or will damage the body during insertion if not surrounded by some introducing means.

Further, it is important to keep the size of these invasive devices as small as possible to create the smallest opening within the body. However, many of the devices introduced have sections which are quite large, principally on a portion of the device located outside of the inserted portion. To pass such a device through an introducer sheath, the introducer sheath must be made with an internal passageway at least as large as the largest part of the device so that the introducer sheath may be removed following device placement in the body. Further, if such enlarged opening is created in the body, when the thin part of the device is advanced, there will now be much empty space creating a pathway for body fluids to pass around the device and escape from the body increasing the risk of clotting, infection, etc.

A device which solves this problem is the peel away introducer sheath used in conjunction with a dilator. The peel away introducer sheath is a thin-walled, usually cylindrical, device that is placed in position so that it provides a communicating passageway through the tissue. This is often accomplished by fitting the introducer sheath tightly over a dilator, advancing both devices through the tissue together as a unit, and then removing the dilator from inside the introducer sheath, leaving the introducer sheath alone in the desired position, acting to hold the penetrated site open. At that point, the catheter tube or other invasive device is advanced through the introducer sheath into the desired position The peel away introducer sheath is then removed from the tissue and pulled apart lengthwise into two pieces. This capacity for splitting allows the introducer sheath to be made as small as the inner compartmental portion of the inserted medical device. The introducer sheath is then pulled apart and removed. Proximal handles on the introducer sheath are generally provided to facilitate grasping of the introducer sheath halves.

Several types of peel away introducer sheaths are known in the prior art. For example, U.S. Pat. No. 4,983,168 discloses a layered peel away hollow sheath wherein the sheath wall is comprised of at least two layers, the inside layer being cylindrical and the outside layer comprising two semi-cylindrical segments defining opposed axially-directed slits or slots there between which comprise tear lines such that the sheath manually tears axially along the single layered tear line into two pieces for removal of the sheath from around the indwelling device.

U.S. Pat. No. 4,596,559 discloses a tear away introducer tool for use with a disposable introducer set in conjunction with a catheter. The tear away introducer is comprised of an elongated sheath having a pair of opposed splits in the proximal end which define a pair of tabs. A handle is secured to the sheath and includes a pair of handle members, each comprising a pair of clamping elements which clamp the tabs of the sheath there between. The handle has opposed weakened portions which facilitate the tearing of the sheath along axial lines.

U.S. Pat. No. RE 31,855 discloses a sheath that has an internal molecular orientation which tears easily in a lengthwise direction and with great difficulty in a crosswise or oblique directions. See also U.S. Pat. No. 4,581,025.

U.S Pat. Nos. 4,166,469, 4,243,050, 4,345,606 and 4,451,256 disclose sheaths longitudinally scored or perforated on opposite sides. This results in a cylindrical sheath with two weakened lines which run lengthwise on opposite sides of the cylinder. The introducer or sheath is thus mechanically weakened along its scored or perforated regions and less resistant to tearing than the rest of the sheath cylinder, causing the tear once started to propagate along the weakened region. See also U.S. Pat. No. 4,451,256.

Regardless of which of these types of peel away introducer sheaths is used, there is a tendency for the dilator to rearwardly migrate into the introducer sheath when the medical practitioner attempts to forcibly enlarge the introduction site by driving the tapered leading edge of the tip of the dilator through the skin and subcutaneous tissue. This tendency makes manipulation not only difficult but also traumatic for the patient.

Further, the introducer sheath may be damaged, requiring use of a new invasive device.

One method of addressing this problem is disclosed in U.S. Pat. No. 4,772,266. Incorporated in the proximal end of the dilator is a female coupling element, the interior of which comprises a helically directed luer loc mechanism. The proximal end of the introducer sheath contains a male luer loc coupling member which works in combination with the female coupling member of the dilator. As the female coupling member is axially rotated around the male coupling member of the introducer sheath, the dilator and the introducer sheath are releasably locked in position. This device is cumbersome to the medical practitioner considering that the practitioner is gloved and manipulation of the device is difficult.

Another method of preventing the undesired migration of the dilator within the introducer sheath is disclosed in U.S. Pat. Nos. 4,243,050 and 4,345,606. In these patents the proximal end of the dilator contains a hub with a lip. The proximal end of the introducer sheath contains a flange, a portion of which fits between the hub and the flange under appropriate circumstances to prevent undesired migration of the dilator within the introducer sheath.

Although not used with a dilator and introducer sheath, U.S. Pat. No. 4,362,156 discloses an intravenous infusion assembly wherein a catheter assembly and a needle assembly are releasably locked together at their proximal ends to prevent relative axial movement there between during insertion into the vein. Clamp arms are an element of the needle assembly wherein said clamp arms contain hooks which engage the lugs on the catheter assembly. Operating in conjunction with the clamp arm and hook are an interfitting tenon on the needle assembly and a notch on the catheter assembly. The combination of all of these elements when interlocked are required to limit relative rotation between the needle assembly and the catheter assembly.

Another method of preventing the migration of the dilator within the introducer sheath is an interlocking mechanism manufactured by Angeion as disclosed in Journal of Invasive Cardiology, Vol. 1, No. 5, p. 249 (1991) and Angeion advertising material of 1991. This mechanism is a one piece device containing an arm which fits below the handle of the introducer sheath and a slotted portion which is secured on the proximal end of the dilator. These two elements working together restrict the dilator from migrating inside the introducer sheath.

Many of the devices previously disclosed provide a method to limited undesirable rearward migration of the dilator into the introducer sheath during the introduction of the dilator within the patient. However, more reliable dilator/introducer sheath assemblies are necessary to prevent problems associated with this migration.

Therefore, it is an object of this invention to provide an improved dilator/introducer sheath set.

It is a further object of this invention to provide an improved dilator/introducer sheath for the unstressed introduction of catheters and other such medical devices into patients.

It is a still further object of the present invention to provide a novel dilator/introducer sheath device which creates a secure relationship between the dilator and introducer sheath to prevent the dilator from rearward migration into the introducer sheath.

These and other objects and features of the present invention will become apparent to those skilled in the art from a consideration of the following detailed description, drawings and claims. The description, along with the accompanying drawings, provide a selected example of the construction of the device to illustrate the invention.

SUMMARY OF THE INVENTION

In accordance with the present invention there is provided a dilator and introducer sheath locking system comprised of a dilator containing an elongated dilator cannula with a tapered distal end, a gripping clamp secured to its proximal end and a peel away introducer sheath with a tapered distal end and a proximal end containing a splittable handle which interacts with the gripping clamp of the dilator to prevent undesired rearward migration of the dilator within the introducer sheath.

This locking dilator and peel away introducer sheath system provides an easy to use, safe method of inserting the introducer and dilator into a patient while maintaining a stable relationship between the dilator and introducer sheath during such introduction. Because of its unique locking mechanism, undesired rearward migration of the dilator within the introducer sheath is eliminated.

BRIEF DESCRIPTION OF THE DRAWINGS

This invention will now be referenced with the following drawings in which

FIG. 1A is a cross-section of the peel away introducer sheath.

FIG. 4 is an exploded view of the peel away introducer sheath.

DETAILED DESCRIPTION OF PREFERRED EMBODIMENT

Figure 1:
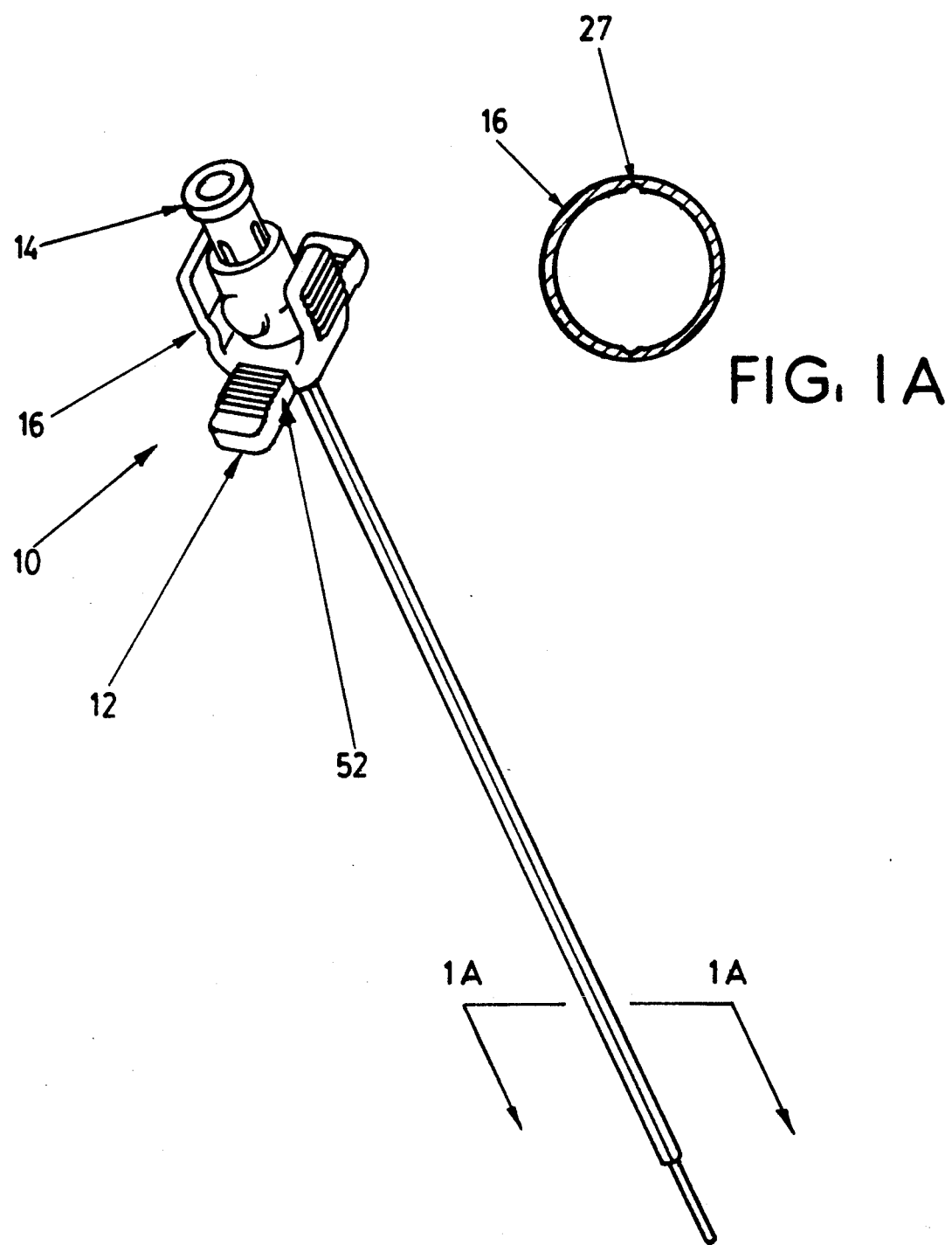
FIG. 1 is a perspective view of the locking dilator and peel away introducer sheath system clamped together by the gripping clamp mechanism.
Figure 2:
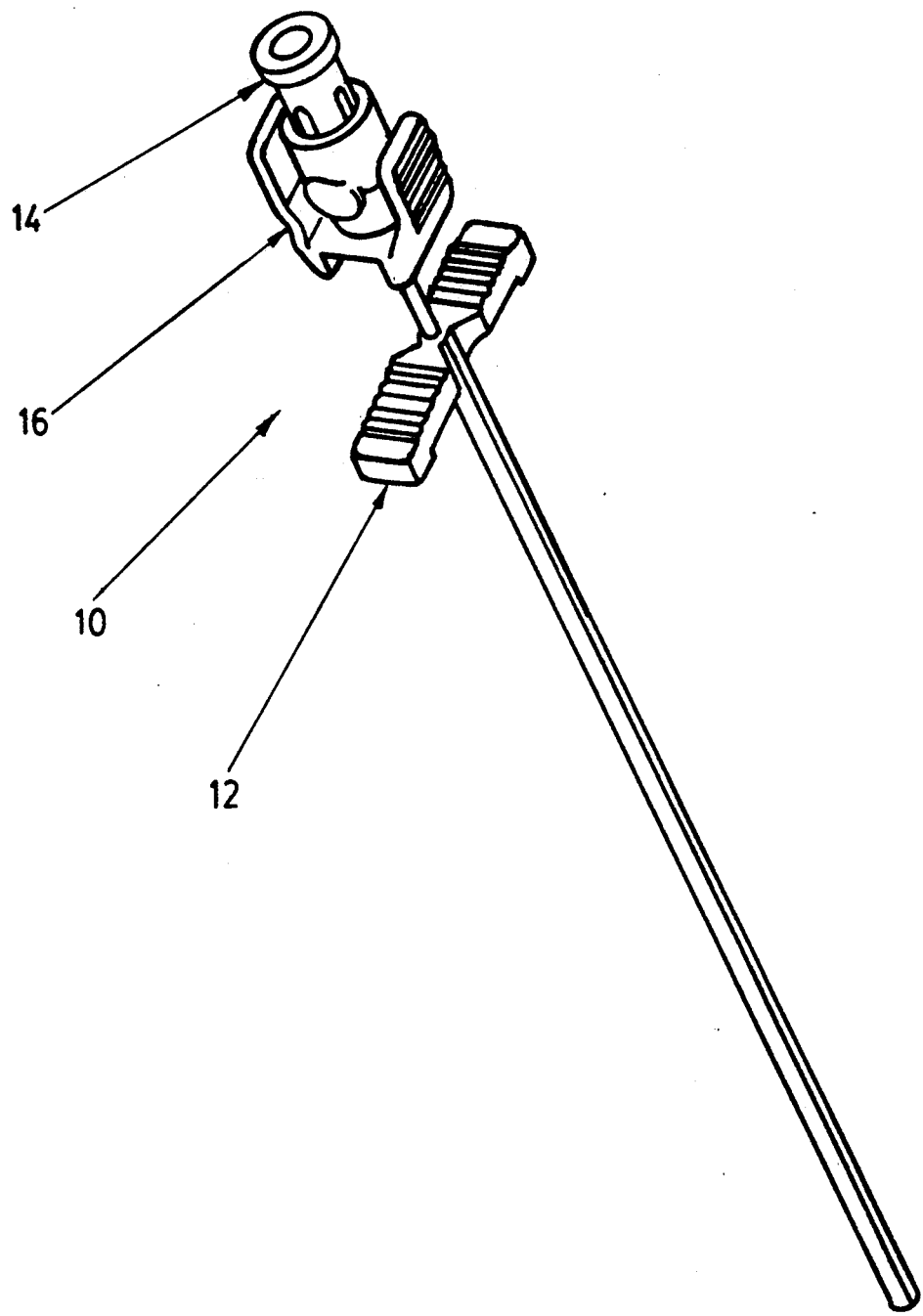
FIG. 2 is a perspective view of the locking dilator with the peel away introducer sheath partially advanced toward the distal end of the dilator.

Although the invention is adaptable to a wide variety of uses, it is shown in the drawings for the purpose of illustration as embodied in a locking dilator with peel away introducer sheath system (10) comprised of a peel away introducer sheath (12) used in combination with a dilator (14) containing a gripping clamp mechanism (16) for securing the dilator (14) and the introducer sheath (12) together to prevent rearward migration of the dilator within the introducer sheath. See FIGS. 1 and 2.

The dilator and introducer sheath are components of an introducer set which commonly includes a disposable syringe, a hollow hypodermic needle for use with the syringe and a wire guide. These products may also be used in other generally accepted introducer placement techniques.

Figure 3:
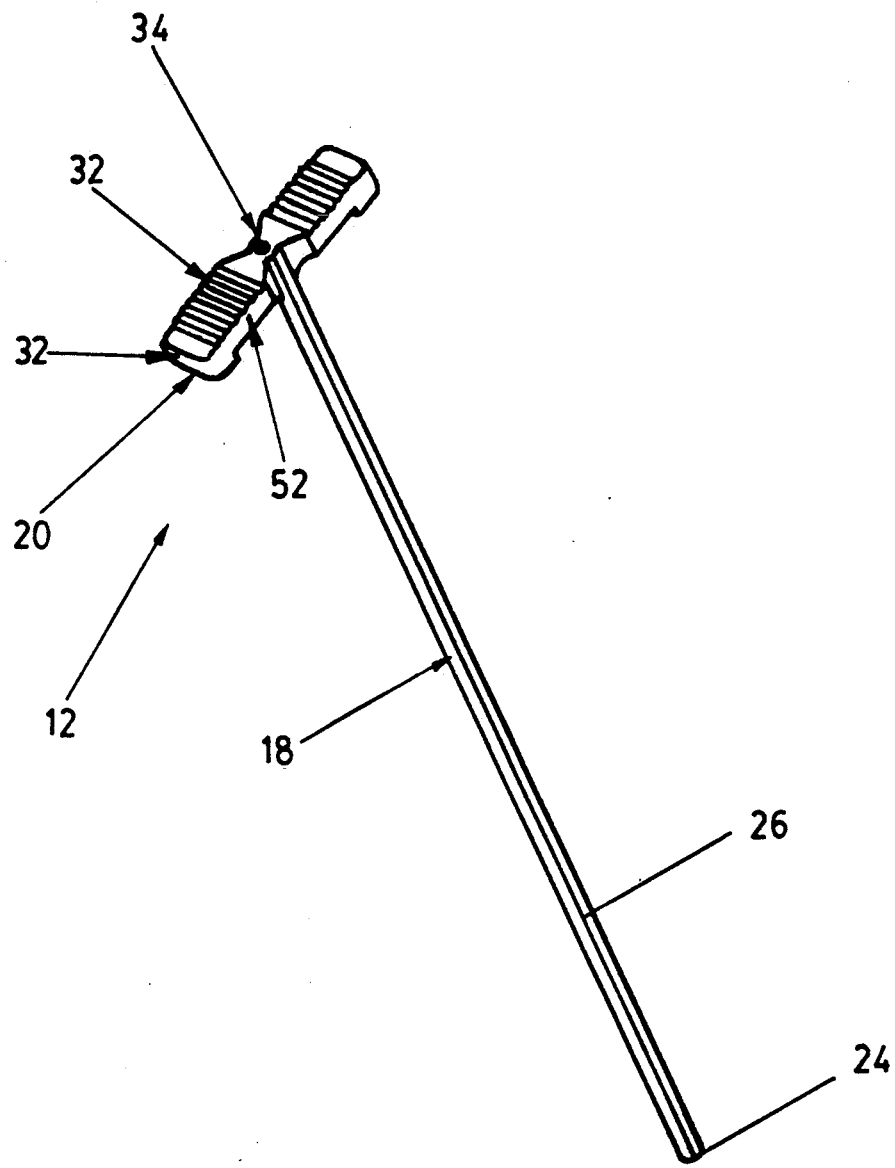
FIG. 3 is a perspective view of the peel away introducer sheath.

The introducer sheath (12) is a generally elongated substantially cylindrical tube (18) having a handle (20) affixed to the proximal end thereof. See FIGS. 3 and 4.

The tube (18) is formed of a suitable plastic, preferably a tetrafluoroethylene, fluorinated ethylene-propylene or polyethylene type plastic, wherein said plastic is compatible with body fluids. The tube has a proximal end (22) and a distal end (24). In addition, the tube has a pair of mechanically formed, longitudinally extending zones (26) of reduced thickness defined by internally scored longitudinal shallow grooves (27) or indentations, running throughout the length of the tube. See FIG. 1A. These mechanically formed, reduced thickness zones permit the introducer sheath to be "peeled away" following use. Although other methods of splitting the introducer sheath are acceptable and well known, the above referred to method is preferred.

The handle (20) includes a pair of handle members (30) which project laterally outward from the cylindrically shaped tube engaging said tube (18). Each handle member (30) is secured to the proximal end (22) of the introducer sheath by conventional securing methods. Each handle member (30) defines one-half of the handle (20). Each of the handle members (30) are secured to the tube (18) at such a location to permit the easy splitting of the tube by pressure on the top surface (32) of each of the handle members as they are pulled away from the surface of the tube. To assist in the easy splitting of the tube, the top surface (32) of each of the handle members is ribbed. The handle members are extended, preferably, at least about ½ inch from the surface of the tube for ease of use. The tube extends proximally to the surface of the handle and creates the dilator opening (34) running the length of the tube through which the dilator can be inserted.

Figure 5:
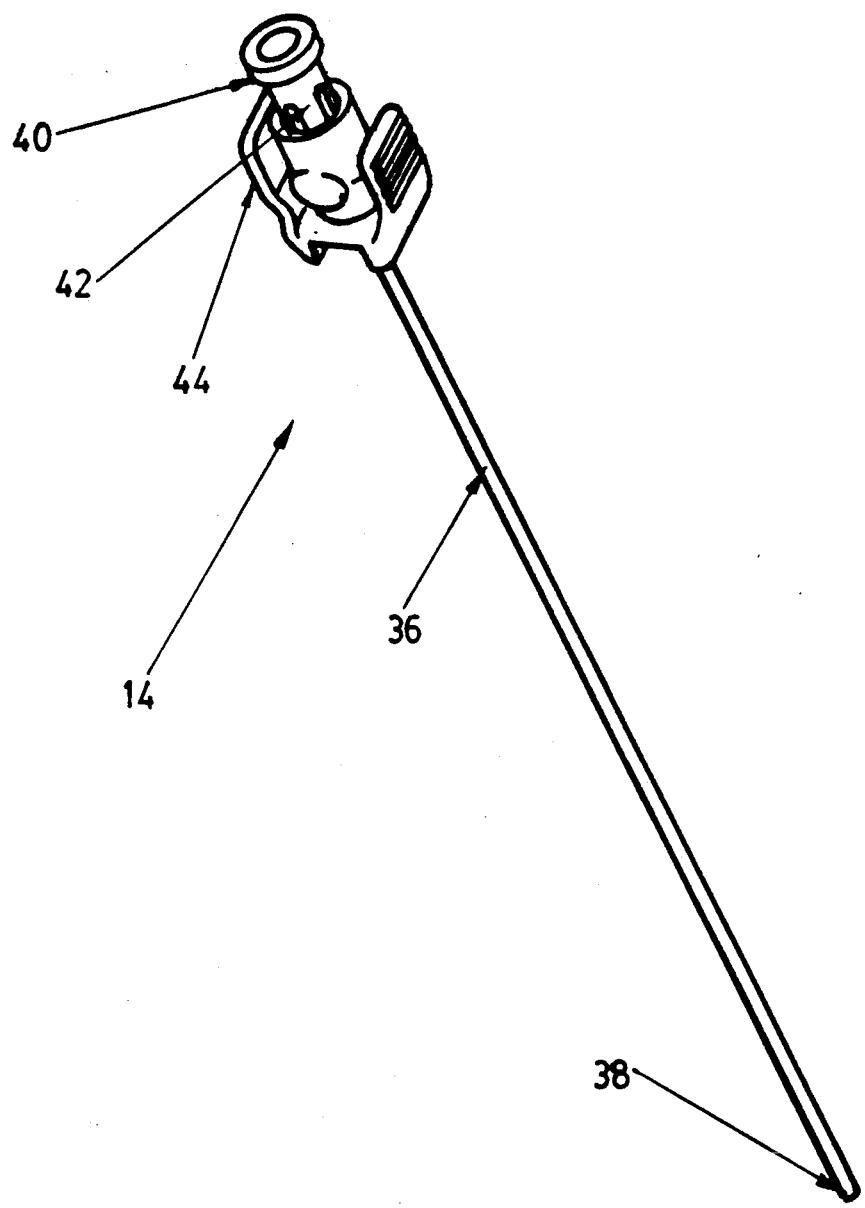
FIG. 5 is a perspective view of the dilator with attached gripping clamp mechanism.

The dilator (14) includes an elongated tubular portion (36) with a tapered distal end (38) also formed of a suitably compatible plastic material. See FIG. 5. The external diameter of the tubular portion of the dilator is of a size sufficient to pass through the dilator opening (34) in the introducer (12).

Attached at the proximal end (40) of the dilator is a Luer fitting (42) which is used in combination with other medical instruments. This fitting (42) is frequently used by a medical practitioners as a support during insertion of the introducer set.

Figure 6:
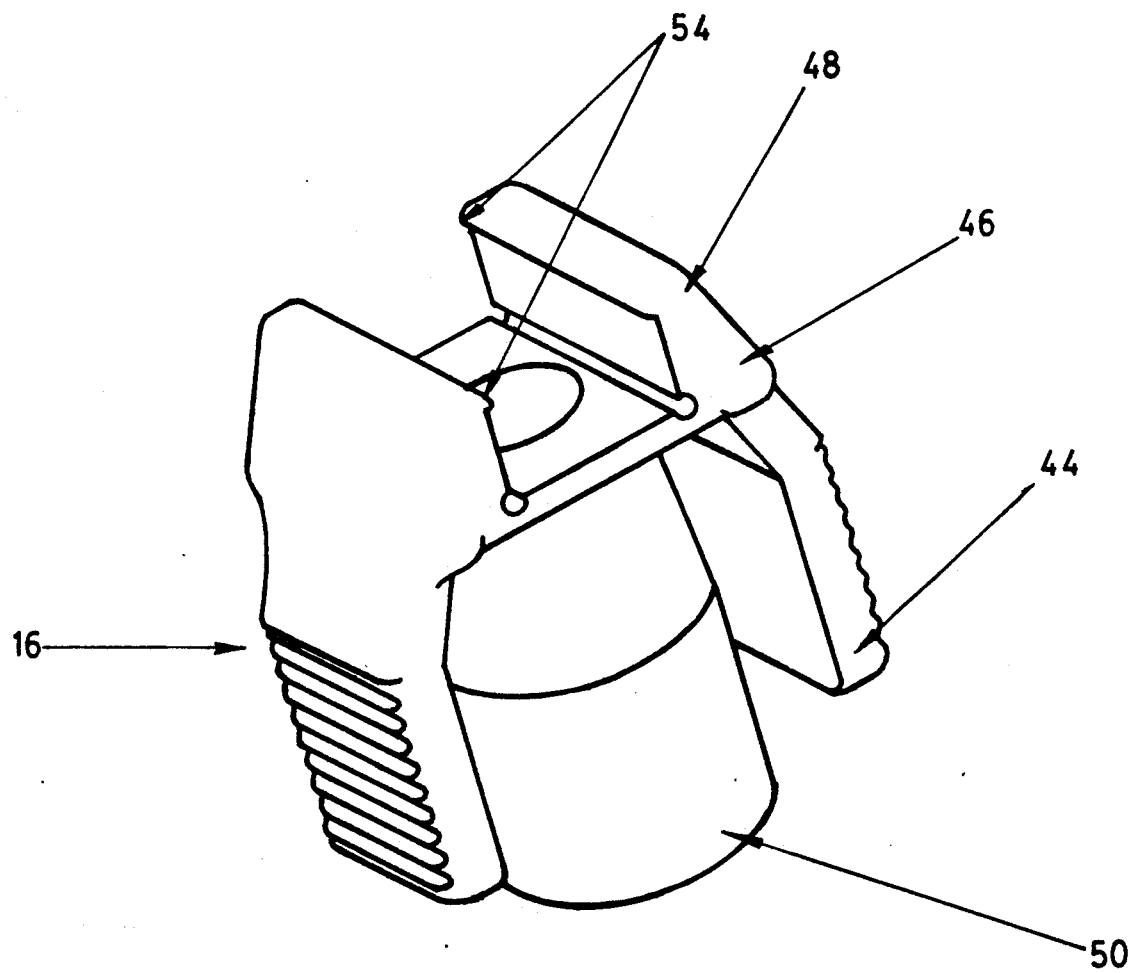
FIG. 6 is a perspective view of the gripping clamp mechanism.

Secured to the proximal end (40) of the dilator around the fitting is the gripping clamp mechanism (16). See FIG. 6. The gripping clamp mechanism (16) is comprised of a pair of arms (44) connected by integral hinges (46) to a pair of proximal clamping sides (48) and a gripping clamp body (50). The arms (44) project away from the distal end of the dilator and preferably are ribbed on their outside surface. The hinges are secured to the gripping clamp body (50) which is preferably tubular in shape and secured by conventional securing means to the Luer fitting (42) of the dilator or may be molded as one piece to the proximal end (40) of the tubular portion (36). The proximal clamping sides (48) project down the dilator to form the pair of opposite faced parallel clamping sides. These proximal clamping sides (48) will, when properly sited, clamp over the side edges (52) of the handle members (30) of the introducer sheath. See FIG. 1. The width of these clamping sides must be sufficient to hold the handle members (30) securely in place. In a preferred embodiment each proximal clamping side (48) will contain a lip (54) to assist in holding the handle members (30) securely in place. See FIG. 6. In one embodiment these lips are on the outside edge of the clamping sides (48) and project over the edge of the side edged (54) of the handle members when in use. Alternatively, the lip interacts with a slot (not shown) in the side edge of the handle member to hold securely the handle member. In a further alternative, a slot (not shown) in the clamping sides interacts with a lip (not shown) in the side edge of each handle member to hold the handle member securely in place.

The pressure of the clamping sides (48) on the handle members (30) and the interaction of the lips (54) of the clamping sides (48) on the side edges (52) of the handle members (30) prevent undesired longitudinal movement of the dilator within the introducer sheath and also prevent the handle members from pulling apart while secured. The introducer sheath is removed from its hold by the gripping clamp mechanism (16) by squeezing on the arms (44) of the gripping clamp mechanism (16).

In operation, the vein of a patient is pierced by a hypodermic needle. The syringe is removed and a guidewire is threaded through the needle into the vein leaving a portion of the guidewire exposed. The needle is thereafter removed from the wire. The dilator with gripping clamp (14) is inserted through the dilator opening (34) in the introducer sheath (12) and the handle members (30) are clamped in place by the clamping sides (48) of the gripping clamp mechanism (16). The combined dilator and introducer sheath are then advanced as a unit over the guidewire and through the skin incision into the vein. The maintenance of the introducer sheath and the dilator at their respective position by use of the gripping clamp mechanism (16) is key to the introduction of the dilator and introducer sheath into the patient. Significant problems have occurred with dilators migrating rearwardly into the orifice of the introducer sheath, resulting in the collapse of the sheath tip and undue trauma to the patient.

After the introducer set has been advanced into the patient, the arms (44) of the gripping clamp mechanism (16) are squeezed to disconnect the dilator (14) from the introducer sheath (12). The dilator (14) and guidewire are then removed and an appropriate medical device, such as a catheter, is passed into the introducer sheath (12). The catheter is advanced through the tube (18) of the introducer sheath into the vein. After the catheter has been properly located, the introducer sheath (12) is withdrawn from the patient The introducer sheath is then removed from the patient by the simultaneous gripping of each of the handle members (30) followed by pulling apart of the tube (18). By pulling the handle members (30) apart, the tube will be split along the zones of reduced thickness (26), resulting in the entire introducer sheath being readily split.

We claim:

1. A dilator and peel away introducer sheath assembly comprising
   (a) a dilator means comprised of an elongated dilator tube means with a tapered distal end and a dilator fitting secured to the proximal end of the elongated dilator tube means;
   (b) a gripping, clamp means secured to said dilator means; and
   (c) a peel away introducer sheath means with tapered distal end and a proximal end containing a splittable handle such that the introducer sheath means may be split along weakened lines through its entire length, wherein said gripping clamp means of said dilator means secures said splittable handle of said introducer sheath means to prevent undesired longitudinal movement of the dilator means when secured to the introducer sheath means by the gripping clamp means and wherein the gripping clamp means when secured to the introducer sheath means prevent the splittable handle of said introducer sheath means from splitting.

2. The dilator and peel away introducer sheath assembly of claim 1 wherein the gripping clamp means is comprised of a pair of arms, an integral hinge, proximal clamping sides and a gripping clamp body.

3. The dilator and peel away introducer sheath assembly of claim 2 wherein the proximal clamping sides are a pair of opposite faced substantially parallel clamping sides directed toward the distal end of the introducer sheath means.

4. The dilator and peel away introducer sheath assembly of claim 3 wherein each opposite faced substantially parallel clamping side contains a lip on its outside edge.

5. The dilator and peel away introducer sheath assembly of claim 4 wherein said lip protrudes over the side of the splittable handle to hold said handle securely in place when the dilator means and introducer sheath means are secured together.

6. The dilator and peel away introducer sheath assembly of claim 2 wherein said splittable handle is released by compressing said pair of arms of said gripping clamp means and sliding said introducer sheath means down said dilator means.

7. The dilator and peel away introducer sheath assembly of claim 2 wherein said outside surface of said arms is ribbed.

8. The dilator and peel away introducer sheath assembly of claim 1 wherein the proximal clamping sides engage the handle members of the introducer sheath means to secure the introducer sheath means and dilator means together.

9. The dilator and peel away introducer sheath assembly of claim 1 wherein the gripping clamp means is secured to the proximal end of the dilator means.

10. A dilator and peel away introducer sheath assembly comprising
  (a) a dilator means;
  (b) a gripping clamp means secured to the proximal end of said dilator means wherein said gripping clamp means is comprised of a pair of arms with a ribbed outside surface, an integral hinge, proximal clamping sides and a gripping clamp body; and
  (c) a peel away introducer sheath means with tapered distal end and a proximal end containing a splittable handle such that the introducer sheath means may be split along weakened lines through its entire length, wherein said gripping clamp means of said dilator means secures said splittable handle of said introducer sheath means to prevent undesired longitudinal movement of the dilator means when secured to the introducer sheath means by the gripping clamp means and wherein the gripping clamp means when secured to the introducer sheath means prevent the splittable handle of said introducer sheath means from splitting.

* * * * *